United States Patent
Hyun et al.

(10) Patent No.: US 8,369,597 B2
(45) Date of Patent: Feb. 5, 2013

(54) NON-RIGID REGISTRATION BETWEEN CT IMAGES AND ULTRASOUND IMAGES

(75) Inventors: Dong Gyu Hyun, Seoul (KR); Jong Beom Ra, Daejeon (KR); Duhgoon Lee, Daejeon (KR); Woo Hyun Nam, Busan (KR)

(73) Assignees: Medison Co., Ltd. (KR); Korea Advanced Institute of Science and Technology (KR)

( * ) Notice: Subject to any disclaimer, the term of this patent is extended or adjusted under 35 U.S.C. 154(b) by 401 days.

(21) Appl. No.: 12/477,081

(22) Filed: Jun. 2, 2009

(65) Prior Publication Data
US 2009/0304252 A1 Dec. 10, 2009

(30) Foreign Application Priority Data
Jun. 5, 2008 (KR) .................. 10-2008-0053225

(51) Int. Cl.
*G06K 9/00* (2006.01)

(52) U.S. Cl. ........ 382/131; 382/132; 382/190; 382/305; 600/443; 600/437; 600/441

(58) Field of Classification Search .......... 382/131–132, 382/154, 190, 275, 264, 305, 294; 600/441, 600/443, 444, 437–439
See application file for complete search history.

(56) References Cited

U.S. PATENT DOCUMENTS

| 8,098,911 B2 * | 1/2012 | Chefd'hotel et al. ......... 382/131 |
| 2005/0004458 A1 | 1/2005 | Kanayama et al. |
| 2006/0004275 A1 * | 1/2006 | Vija et al. ..................... 600/407 |
| 2007/0167784 A1 * | 7/2007 | Shekhar et al. ............... 600/443 |
| 2008/0009724 A1 | 1/2008 | Lee et al. |
| 2008/0123927 A1 * | 5/2008 | Miga et al. ..................... 382/131 |

FOREIGN PATENT DOCUMENTS

| KR | 10-2006-0080562 A | 7/2006 |
| KR | 10-2007-0110965 A | 11/2007 |
| KR | 10-2008-0053057 A | 6/2008 |

OTHER PUBLICATIONS

Korean Notice of Allowance, issued in Korean Patent Application No. 10-2009-0050039, dated Jul. 20, 2011.

(Continued)

*Primary Examiner* — Gregory J Toatley
*Assistant Examiner* — Iyabo S Alli
(74) *Attorney, Agent, or Firm* — McDermott Will & Emery LLP

(57) ABSTRACT

There are disclosed embodiments for non-rigid image registration between 3-dimensional ultrasound and CT images by using intensity and gradient information of vessels and diaphragm. An ultrasound image forming unit transmits/receives ultrasound signals to/from a target object to thereby output electrical receive signals, and forms 3-dimensional ultrasound images based on the electrical receive signals. A CT image forming unit forms 3-dimensional CT images of the target object. A registration unit determines first and second objective functions associated with diaphragm and vessel regions of the target object, respectively, based on intensity and gradient information upon portions corresponding to the diaphragm and vessel regions in each of the 3-dimensional ultrasound and CT images. The registration unit performs non-rigid image registration between the 3-dimensional ultrasound images and the 3-dimensional CT images based on the first and second objective functions.

9 Claims, 2 Drawing Sheets

OTHER PUBLICATIONS

Nam et al., "Anatomical feature extraction in 3D B-mode ultrasound liver images for CT-ultrasound image registration," *Int J CARS*, 2008,3(Suppl 1): S401-S402.

Extended European Search Report issued in European Patent Application No. 09161545.0, dated Sep. 5, 2011.

Pitiot et al., "Piecewise Affine Registration of Biological Images for Volume Reconstruction," Medical Image Analysis, Elsevier, 19 pages (Received Aug. 9, 2004).

\* cited by examiner

NON-RIGID REGISTRATION BETWEEN CT IMAGES AND ULTRASOUND IMAGES

The present application claims priority from Korean Patent Application No. 10-2008-0053225 filed on Jun. 5, 2008, the entire subject matter of which is incorporated herein by reference.

TECHNICAL FIELD

The present disclosure relates to image registrations, and more particularly to a non-rigid image registration between 3-dimensional computerized-tomography (CT) images and 3-dimensional ultrasound images based on the intensity and gradient information thereof.

BACKGROUND

An ultrasound diagnostic system has been extensively used in the medical field due to its non-invasive and non-destructive nature. The ultrasound diagnostic system is highly safe and produces no dangerous side effects such as exposure to X-rays, etc. However, the ultrasound diagnostic system suffers from inherent shortcomings of an ultrasound image such as a low signal-to-noise ratio and a limited field of view. Thus, the image registration of a CT (or MR) image onto the ultrasound image has been introduced in order to compensate for deficiencies of the ultrasound image.

The image guided intervention is one of the medical applications, which require the image registration between intra-operative and preoperative images. In case of the liver, a 3-dimensional ultrasound image is frequently used for the image-guided intervention. However, due to the poor quality of the 3-dimensional ultrasound image, it is required to display a preoperative 3-dimensional CT (or MR) image, which corresponds to an intraoperative 3-dimensional ultrasound image, but whose quality is relatively high compared thereto. In such a case, the image registration between the 3-dimensional ultrasound image and the 3-dimensional CT image is necessary. The 3-dimensional ultrasound image and the 3-dimensional CT image are formed at different respirations so that local deformation may appear. Thus, a non-rigid image registration, which is an essential step in various medical applications for image registration, should be performed.

However, it is a difficult task to register the 3-dimensional CT image onto the 3-dimensional ultrasound image due to their different imaging characteristics. Several algorithms have been proposed for performing the non-rigid image registration between the 3-dimensional ultrasound and CT (or MR) liver images. For theses image registration, the 3-dimensional ultrasound and CT (or MR) images are converted into vessel probability images. Thereafter, a normalized cross correlation between two vessel probability images is maximized. Also, the image registration method between the 3-dimensional ultrasound and CT (or MR) images, which is performed by extracting and registering centerlines of vessels, has been proposed. In such a method, however, the registration accuracy may depend on vessel segmentation accuracy in the 3-dimensional ultrasound and CT (or MR) images.

SUMMARY

An embodiment for a non-rigid image registration between 3-dimensional ultrasound and CT images is disclosed herein. In one embodiment, by way of non-limiting example, a system for non-rigid image registration between ultrasound images and computerized tomography (CT) images, comprises: an ultrasound image forming unit configured to transmit/receive ultrasound signals to/from a target object to thereby output electrical receive signals, and form 3-dimensional ultrasound images based on the electrical receive signals; a CT image forming unit configured to form 3-dimensional CT images of the target object; and a registration unit configured to determine first and second objective functions associated with first and second regions of the target object, respectively, based on the intensity and gradient information upon portions corresponding to the first and second regions in each of the 3-dimensional ultrasound and CT images, and perform non-rigid image registration between the 3-dimensional ultrasound images and the 3-dimensional CT images based on the first and second objective functions.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

In one embodiment, vessel and diaphragm information may be used for a non-rigid registration between computerized-tomography (CT) and ultrasound images of a target object. Although the CT image is referred to as an example of medical images registered onto the ultrasound images, the medical image is certainly not limited thereto. The medical images may also include a magnetic resonance imaging (MRI) image, positron emission tomography (PET) image and the like. In one embodiment, the target object may be a liver, although it is certainly not limited thereto. For robust and accurate registration, a new objective function based on a 3-dimensional joint histogram of intensity and gradient information, which is obtained from the ultrasound and CT images, may be adopted.

In one embodiment, the non-rigid registration may be adopted to register affine-registered 3-dimensional ultrasound and CT images. Two features of the liver, i.e., features of vessels and a diaphragm, may be utilized for the registration. To find an accurate transformation for the non-rigid registration, a cost function may be defined by using objective functions of two features. In one embodiment, the cost may be minimized through an optimization process.

Figure 1:
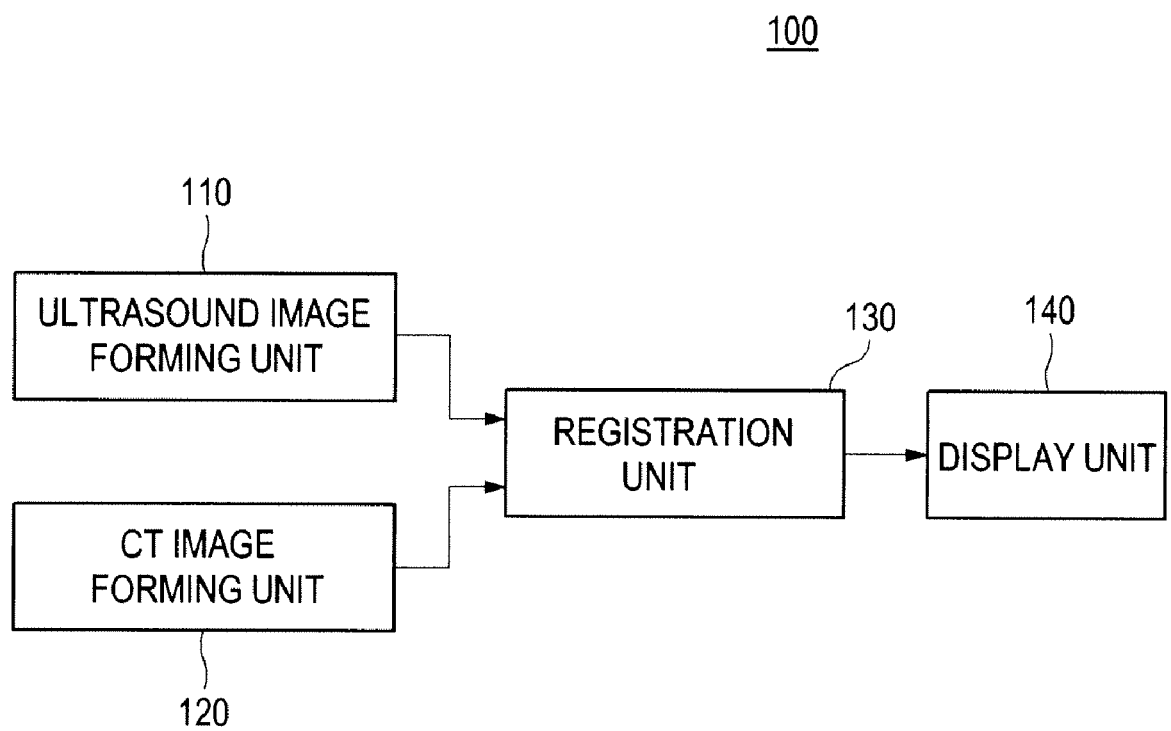
FIG. 1 is a block diagram showing an illustrative embodiment of a system for a non-rigid registration between the 3-dimensional ultrasound images and the 3-dimensional CT images.

FIG. 1 is a block diagram showing an illustrative embodiment of a system for the non-rigid registration between the 3-dimensional ultrasound images and the CT images. As depicted in FIG. 1, the system 100 may include an ultrasound image forming unit 110. The ultrasound image forming unit 110 may be configured to transmit/receive ultrasound signals to/from the target object to thereby output electrical receive signals. The ultrasound image forming unit 110 may be further configured to form ultrasound images of the target object based on the electrical receive signals. The ultrasound images may include a 3-dimensional ultrasound image obtained in a brightness mode (B-mode).

The system 100 may further include a CT image forming unit 120. The CT image forming unit may be configured to form 3-dimensional CT images of the target object. In one embodiment, each of the 3-dimensional ultrasound images and the 3-dimensional CT images may be obtained at different respirations. The system 100 may further include a registration unit 130 that may be operable to perform a non-rigid registration between the 3-dimensional ultrasound images and the 3-dimensional CT images based on the intensity and gradient information thereof. The operations of the registration unit 130 will be described in detail with reference to FIG. 2.

Figure 2:
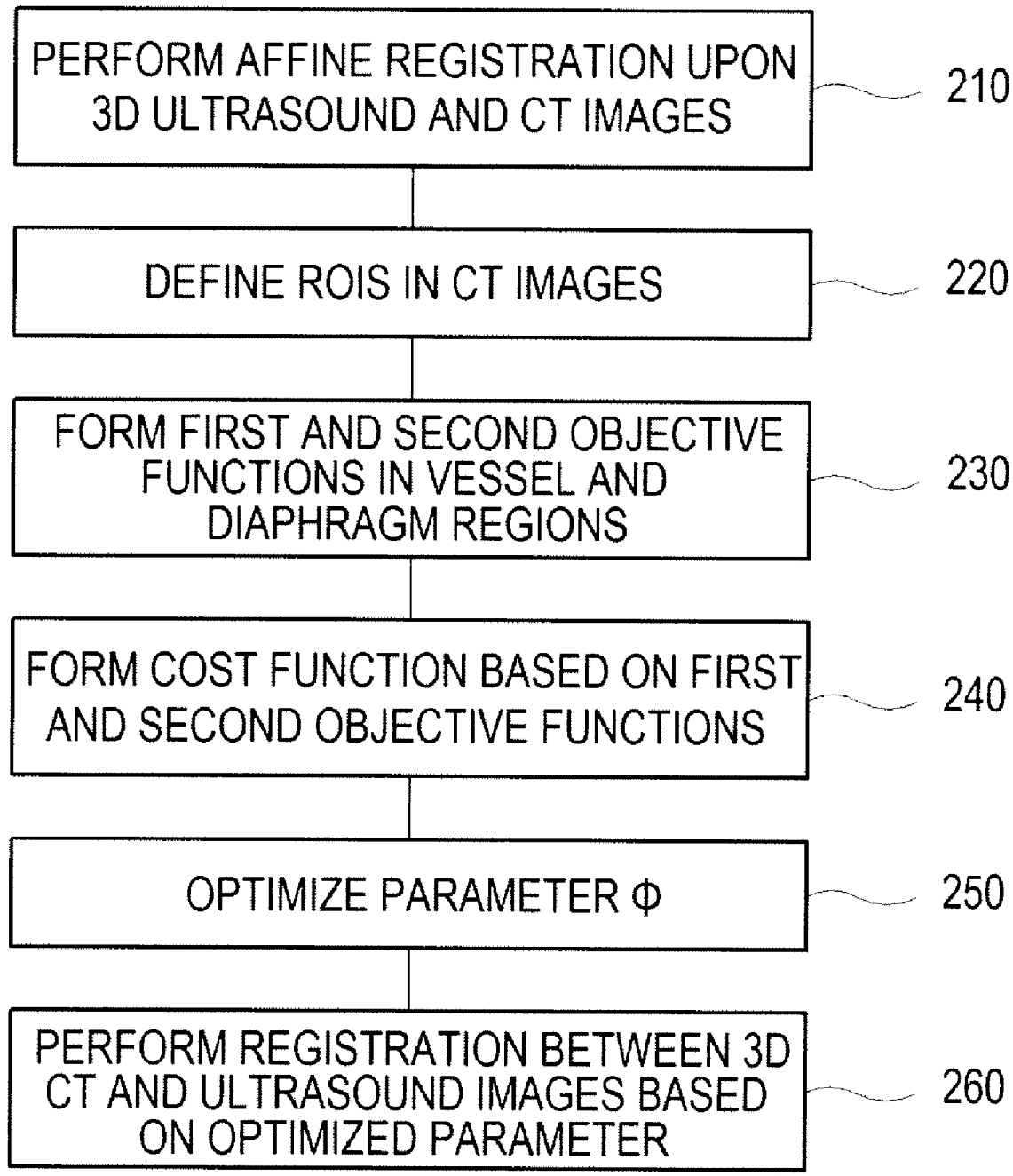
FIG. 2 is a flowchart showing a non-rigid image registration procedure between the 3-dimensional ultrasound images and the CT images.

FIG. 2 is a flowchart showing a non-rigid image registration procedure between the 3-dimensional ultrasound images and the CT images. Referring to FIG. 2, the Iterative Closest Point (ICP)-based affine registration upon the 3-dimensional ultrasound images and the 3-dimensional CT images may be performed at block 210.

In one embodiment, the B-spline free form deformation (FFD) may be adopted as a transformation in order to model a local deformation between the 3-dimensional ultrasound images and the 3-dimensional CT images. The transformation may be defined by displacements of control points having a uniform interval. The displacements may be represented with a transformation parameter $\Phi$. In one embodiment, the local deformation may be expected to be smooth over the liver so that the local deformation may be estimated by the smooth transformation. Hence, constraint $C_{smooth}$ may be defined and used as a 3-dimensional counterpart of 2-dimensional bending energy of a thin-plate of metal.

The intensity relationships between vessels and a diaphragm in the ultrasound image and the CT image are quite different. In the ultrasound image, the diaphragm may appear at a relatively high intensity due to the strong reflection of an ultrasound signal. This characteristic of the diaphragm in the ultrasound image may be associated with the diaphragm represented with a high gradient magnitude in the CT image. Further, intensity values of a vessel region in the ultrasound image may be associated with those of the CT image, even though the contrast of the CT image is reversed. Thus, the objective function may be differently evaluated between the diaphragm and the vessel regions. While the first objective function $C_{diaphragm}$ in the diaphragm region may be obtained by using the intensity values of the ultrasound image and the gradient magnitudes of the CT image, the second objective function $C_{vessel}$ in the vessel region may be obtained by using intensity values of the ultrasound image and the CT image.

To evaluate the objective functions in the diaphragm and vessel regions, a plurality of regions of interest (ROIs) may be defined in the CT image at block 220. The vessels and liver tissues in the CT image may be segmented by using the region-growing scheme. Thereafter, edge regions of segments may be expanded with a predetermined margin to thereby define the ROIs. In one embodiment, since computation necessary for the registration is carried out only upon overlapping portions of the ultrasound image and the CT image, it is sufficient to define the ROIs at one of the ultrasound image and the CT image. In one embodiment, the ROIs may be defined in the CT image, which provides relatively clearer boundaries of the vessels and the liver tissues than the ultrasound image. ROI masking may be carried out upon the vessel region and the diaphragm region in order to define the ROIs. This is to enable the CT image to be segmented into two regions, i.e., the vessel region and the diaphragm region through the ROI masking.

Subsequently, an objective function $C_{diaphragm}$ in the diaphragm region and an objective function $C_{vessel}$ in the vessel region may be formed at block 230. For robust and accurate registration, in one embodiment, the objective functions may be computed based on intensity values, gradient magnitudes and edge orientation angles in the ultrasound image and the CT image.

The gradient magnitudes and the edge orientation angles may be computed as explained below. First, a structure matrix may be computed from each of the voxels constituting the ultrasound image and the CT image. Eigenvectors and eigenvalues may be extracted through an eigen-analysis of the structure matrix. In such a case, the eigenvector with the largest eigenvalue may be defined as an edge orientation of the image, while the gradient magnitudes may be defined using the eigenvalue. If two images are perfectly registered onto each other, then the corresponding edge orientation angles may be identical to each other. Based on this relationship, an edge orientation coincidence function may be defined as a square of an inner product of two edge orientation vectors.

The objective function $C_{vessel}$ may be determined based on mutual relationships between intensity values of the ultrasound image and the CT image in the vessel region. To determine the objective function $C_{vessel}$, statistical entropy may be measured by using the intensity values of the ultrasound image, the intensity values of the CT image and the edge orientation coincidence function.

Also, the objective function $C_{diafragm}$ may be determined based on mutual relationships between the intensity values of the ultrasound image and the gradient magnitudes of the CT image in the diaphragm region. To determine the objective function $C_{diafragm}$, statistical entropy may be measured by using the intensity values of the ultrasound image, the gradient magnitudes of the CT image and the edge orientation coincidence function.

Subsequently, a cost function may be defined with two objective functions $C_{vessel}$ and $C_{diaphragm}$ as following equation (1) at block 540.

$$C = C_{vessel} + C_{diaphragm} + \lambda \cdot C_{smooth} \tag{1}$$

wherein $\lambda$ is a weighting value representing tradeoff between alignment of two images and smoothness of the transformation $C_{smooth}$. The transformation parameter $\Phi$ may be optimized at block 250. In one embodiment, the gradient descent scheme may be utilized to find the optimized transformation parameter $\Phi$. The transformation parameter $\Phi$ may be updated by using the gradient of the cost function as following equation (2).

$$\Phi_{k+1} = \Phi_k + \mu \cdot \nabla C \tag{2}$$

wherein $\mu$ denotes a block size and k is a natural number representing a repetition status of the gradient descent. $\nabla C$ may be approximated to a finite difference of the cost for implementation. If the following equation (3) is satisfied for a small positive value of $\epsilon$, then the optimization process may be terminated.

$$|C_k - C_{k-1}| < \epsilon \tag{3}$$

Finally, a CT image may be transformed into an ultrasound image by using the optimized transform parameter $\Phi$ to thereby produce a registered CT image onto the ultrasound image at block 260.

The system 100 may further include a display unit 140. The display unit 140 may display the 3-dimensional ultrasound images, 3-dimensional CT images, registered ultrasound-CT images and the like.

As mentioned above, as the objective function using the intensity and gradient information of the 3-dimensional ultrasound and CT images are adopted in one embodiment, the precise registration of the target object may be expected. Also, since the registration of the 3-dimensional CT image onto the 3-dimensional ultrasound image can be implemented regardless of local deformation, it may be useful for ultrasound guided intervention.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A system for a non-rigid image registration between ultrasound images and computerized tomography (CT) images, comprising:
    an ultrasound image forming unit configured to transmit/receive ultrasound signals to/from a target object having a first region and a second region to thereby output electrical receive signals, the ultrasound image forming unit being further configured to form 3-dimensional ultrasound images based on the electrical receive signals;
    a CT image forming unit configured to form 3-dimensional CT images of the target object; and
    a registration unit configured to measure a first statistical entropy based on intensity values in the first region of the 3-dimensional ultrasound images, gradient magnitudes in the first region of the CT images and an edge orientation coincidence function in the first region to determine a first objective function and to measure a second statistical entropy based on intensity values in the second region in each of the 3-dimensional ultrasound and CT images and an edge orientation coincidence function in the second region to determine a second objective function, the registration unit being further configured to perform the non-rigid image registration between the 3-dimensional ultrasound images and the 3-dimensional CT images based on the first and second objective functions.

2. The system of claim 1, wherein the 3-dimensional ultrasound and CT images are 3-dimensional ultrasound and CT liver images, and wherein the first and second regions are diaphragm and vessel regions, respectively.

3. The system of claim 2, wherein the registration unit is configured to:
    perform an affine registration between the 3-dimensional ultrasound images and the 3-dimensional CT images;
    model a local deformation appearing at the affine-registered 3-dimensional ultrasound and CT images to define a transformation parameter;
    define a plurality of regions of interest (ROIs) in the 3-dimensional CT images;
    determine the first objective function in the diaphragm region and the second objective function in the vessel region within the ROIs, define a cost function based on the first and second objective functions;
    perform optimization for updating the transformation parameter based on the cost function; and
    form transformed CT images based on the optimized transformation parameter and perform non-rigid image registration upon the transformed CT images and the ultrasound images.

4. The system of claim 3, wherein the affine registration is carried out based on Iterative Closest Point.

5. The system of claim 3, wherein the local deformation is modeled by imposing B-spline free foam deformation on the affine-registered 3-dimensional ultrasound and CT images.

6. The system of claim 3, wherein the first and second objective functions are formed based on a 3-dimensional joint histogram based on edges orientation angles.

7. The system of claim 6, wherein the ROIs are formed by segmenting vessels and tissues with a region-growing scheme and expanding edge regions of segments with a predetermined margin.

8. The system of claim 6, wherein the cost function is defined by using first and second objective functions $C_{diaphragm}$ and $C_{vessel}$ as following equation:

$$C = C_{vessel} + C_{diaphragm} + \lambda \cdot C_{smooth}$$

wherein $\lambda$ is a weighting value representing tradeoff between alignment of two images and smoothness of the transformation $C_{smooth}$.

9. The system of claim 8, wherein the transformation parameter $\Phi$ is updated by repeatedly performing $\Phi_{k+1} = \Phi_k + \mu \cdot \nabla C$ until $|C_k - C_{k-1}| < \epsilon$ is satisfied, wherein $\mu$ denotes a block size, k is a natural number representing a repetition status of gradient descent and $\epsilon$ is a predetermined small positive value.

* * * * *